(12) United States Patent
Auerswald et al.

(10) Patent No.: US 9,274,080 B2
(45) Date of Patent: Mar. 1, 2016

(54) ELECTROCHEMICAL MEASURING PROBE, FILLING ARRANGEMENT AND MAINTENANCE SYSTEM

(75) Inventors: Lothar Auerswald, Dobeln (DE);
Christian Fanselow, Geringswalde (DE)

(73) Assignee: ENDRESS + HAUSER CONDUCTA GESELLSCAHFT FUR MESS- UND REGELTECHNIK MBH + CO. KG, Gerlingen (DE)

( * ) Notice: Subject to any disclaimer, the term of this patent is extended or adjusted under 35 U.S.C. 154(b) by 902 days.

(21) Appl. No.: 12/971,014

(22) Filed: Dec. 17, 2010

(65) Prior Publication Data
US 2011/0147213 A1   Jun. 23, 2011

(30) Foreign Application Priority Data
Dec. 21, 2009   (DE) .......................... 10 2009 055 092

(51) Int. Cl.
*G01N 27/30* (2006.01)
*G01N 27/36* (2006.01)
*G01N 27/403* (2006.01)

(52) U.S. Cl.
CPC ................ *G01N 27/36* (2013.01); *G01N 27/30* (2013.01); *G01N 27/4035* (2013.01)

(58) Field of Classification Search
CPC ... G01N 27/32; G01N 27/301; G01N 27/302; G01N 27/36; G01N 27/333–27/401; G01N 27/4035
USPC .................................. 204/416–420, 433, 435
See application file for complete search history.

(56) References Cited

U.S. PATENT DOCUMENTS

| | | | | |
|---|---|---|---|---|
| 2,204,120 | A * | 6/1940 | Coberly | 91/282 |
| 2,768,135 | A * | 10/1956 | Adelson | 204/402 |
| 3,530,056 | A * | 9/1970 | Haddad | 204/435 |
| 7,632,385 | B2 * | 12/2009 | Ehrismann | 204/435 |
| 2003/0150726 | A1 * | 8/2003 | West et al. | 204/433 |
| 2009/0096458 | A1 * | 4/2009 | Fanselow et al. | 324/425 |
| 2009/0139469 | A1 * | 6/2009 | Cerny et al. | 123/3 |

FOREIGN PATENT DOCUMENTS

| | | |
|---|---|---|
| DE | 31 00 302 A1 | 12/1981 |
| DE | 39 40 948 A1 | 6/1991 |
| DE | 20 2006 017 215 U1 | 3/2007 |
| DE | 10 2008 055 082 A1 | 7/2010 |

* cited by examiner

*Primary Examiner* — Bach Dinh
(74) *Attorney, Agent, or Firm* — Bacon & Thomas, PLLC (57) ABSTRACT

An electrochemical, measuring probe, for measuring a chemical or physical, measured variable, of a measured medium, wherein the measuring probe comprises: at least one measuring half cell and at least one reference half cell, and the reference half cell includes: a housing of electrically insulating material, in which a reference electrolyte chamber containing a liquid, reference electrolyte is formed, and which has in a housing wall a diaphragm permeable for the reference electrolyte for providing electrolytic contact between the reference half cell and the measured medium; a potential indicating element extending into the reference electrolyte; and a supply opening opening into the reference electrolyte chamber for supply of reference electrolyte into the reference electrolyte chamber. The reference half cell has a check valve blocking exit of reference electrolyte from the reference electrolyte chamber through the supply opening, especially a check valve arranged at least partially within the supply opening.

20 Claims, 3 Drawing Sheets

ELECTROCHEMICAL MEASURING PROBE, FILLING ARRANGEMENT AND MAINTENANCE SYSTEM

TECHNICAL FIELD

The invention relates to an electrochemical measuring probe, especially a potentiometric, measuring probe, for measuring a chemical or physical, measured variable, especially a pH value, of a measured medium, and having at least one measuring half cell and at least one reference half cell.

BACKGROUND DISCUSSION

Reference half cells serve in electrochemical measuring probes, for example, in measuring probes of potentiometric sensors, to deliver a constant reference potential for measurements with one or a plurality of measuring half cells. They are frequently applied in many fields of application as rod-shaped reference electrodes or combined with a measuring electrode to form a so-called single-rod, measuring chain. Measuring electrodes, with which the reference electrodes are applied in combination, are, for example, pH glass electrodes, pH semiconductor electrodes or ion-selective electrodes for determining concentration of cations, such as sodium, potassium, calcium, or anions, such as chloride, fluoride, nitrate and carbonate, in a measured medium. Such electrode combinations serve, for example, for determining corresponding ion concentrations in aqueous solutions or water-containing, measured media, such as natural waters, swimming pools, waste waters or product streams.

It is known, that that part of the reference electrode or reference half cell, which is brought in contact with a measured medium in performing the determining must assure an electrolytic contact of the reference electrolyte located in the reference electrode with the measured medium. The terminology, "electrolytic contact", means here a liquid contact between the reference electrolyte of the reference electrode and the measured medium, such that an exchange of ionic charge carriers is permitted. Such a contact can be accomplished by a diaphragm arranged in the housing wall of the reference half cell for permitting diffusion both from the reference electrolyte into the measured medium as well as also in the opposite direction. The term, "diaphragm", refers here to any contact location allowing such a diffusion. This can be formed, for example, by a ceramic, synthetic material or plastic body, a plug of crosslinked hydrogel, a slit, one or a number of bores, or a ground glass.

Reference electrodes comprise, typically, a reference electrolyte accommodated in a reference electrolyte chamber. Such is frequently an aqueous KCl solution, into which extends a potential indicating element coated with a difficulty soluble salt of the reference electrolyte, e.g. a silver wire coated with AgCl. In the case of such reference electrodes, basically, there is the problem that they do not really have a constant potential, this being due to diffusion processes at the diaphragm, i.e. through diffusion of the reference electrolyte accommodated in the reference electrolyte chamber into the measured medium or from diffusion of the measured medium into the reference electrolyte. Furthermore, also a plugging of the diaphragm is possible, for example, through the crystallizing of difficulty soluble salts. This likewise influences the stability of the potential of the reference electrode.

An opportunity for improving the stability of the potential is to supply the reference half cell with a positive pressure relative to the environment of the reference half cell housing. Reference electrolyte then flows through the diaphragm into the environment, e.g. into the measured medium, into which the reference half cell extends during measurement operation. In this way, on the one hand, continuously very small amounts of reference electrolyte enter into the measured medium, while, on the other hand, the reference half cell remains in proper condition and the diaphragm is cleaned and internally rinsed by the continuous flow of electrolyte solution. Thus, clogging of the diaphragm or a poisoning of the reference electrolyte by substances diffusing from the measured medium into the interior of the reference electrolyte chamber is effectively prevented or at least markedly delayed.

The positive pressure can result from the hydrostatic pressure of the liquid column of the reference electrolyte within the reference electrode. Since the reference electrolyte continuously escapes from the reference electrode, correspondingly, either a relatively large liquid electrolyte reservoir is required within the reference electrode or else there must be a regular refilling of reference electrolyte solution into the reference half cell.

In DE 20 2006 017 215 U1, measuring probes with glass electrodes for pH measuring are described, which have a refillable electrolyte reservoir, also referenced as a paunch or bladder, for accommodating liquid electrolyte. The electrolyte reservoir has an opening, through which a pressurizing medium can enter into the electrolyte reservoir, so that a continual flow of the electrolyte from a diaphragm is assured, in order to avoid penetration of measured medium into the electrode interior. As described in DE 20 2006 017 215 U1, such electrodes require special assemblies, by means of which they can be connected to a process container. An opportunity, in situ, i.e. during measurement operation, to replenish electrolyte into the electrolyte reservoir, is not provided.

In DE 20 2005 009 297 U1, a coupling apparatus for a reference electrolyte supply from an external supply to a reference media container of a potentiometric sensor is described. The coupling apparatus includes a first supply side, coupling body and a second sensor side, coupling body connectable releasably mechanically therewith. Each of the coupling bodies has a reference electrolyte duct, wherein the reference electrolyte duct of the second coupling body is sealed by means of an elastic sealing element. The first coupling body has a hollow needle, which, when the coupling bodies are mechanically connected with one another, pierces through the sealing element, in order to assure a flow connection between the two reference electrolyte ducts of the two coupling bodies sealed relative to the environment. If the coupling bodies are separated from one another, the sealing element should reduce leakage of reference electrolyte from the potentiometric sensor.

The handling of the coupling apparatus described in DE 20 2005 009 297 U1 is, indeed, simple and little susceptible to error. However, in the connecting and separating of the coupling bodies, a leakage of electrolyte from the supply side coupling element is not suppressed, so that there is the danger of a contamination of the environment, or a service person, by escaping reference electrolyte. On the whole, construction of the coupling apparatus is relatively complicated, which correspondingly increases the piece costs of the individual potentiometric sensors.

In DE 39 40 948 A1, a method for continuous electrolyte supply to a reference electrode system and a corresponding reference electrode system are described. In such case, an electrode insert held sealed in an outer seating tube and removable from the seating tube is provided, wherein, by the removal motion, an inner valve mechanism is closed, through which otherwise the liquid, reference electrolyte is fed via the outer seating tube to the electrode insert. In the case of the reversed introductory movement of the electrode insert, the valve mechanism is reopened. The structure of the valve mechanism includes a tube insert connected with the outer seating tube and provided with an electrolyte supply duct, relative to which a rotary sleeve coupled with the electrode insert via a driving pin is rotatable upon removal, or introduction, of the electrode insert. Through the twisting of a transverse bore in the rotary sleeve relative to the electrolyte supply duct in the tube insert upon the removal, or introductory, movement, a connection between the electrolyte supply duct and the interior of the electrode insert is interrupted, or produced, as the case may be.

The described mechanism is very complicated and complex to manufacture. Furthermore, in the case of removal of the electrode insert, only the electrolyte supply relative to the environment is sealed; the opening of the electrode insert, via which electrolyte is fed into the electrode interior, remains, however, open. Thus, also in the case of this construction, the risk of leakage is not excluded in satisfactory manner.

SUMMARY OF THE INVENTION

It is, thus, an object of the invention, to provide an electrochemical, especially a potentiometric, measuring probe having a reference half cell with liquid, reference electrolyte and a filling arrangement for replenishing reference electrolyte into the reference half cell of the measuring probe, such that the disadvantages of the state of the art are overcome. Especially, the measuring probe should provide a replenishment option for escaping reference electrolyte, in given cases, under pressure, while, at the same time, exhibiting simple operability and reduced leakage risk.

This object is achieved by an electrochemical, especially potentiometric, measuring probe for measuring a chemical or physical, measured variable, especially a pH value, of a measured medium, wherein the measuring probe comprises: A measuring half cell and a reference half cell,
wherein the reference half cell includes:
 a housing of electrically insulating material, in which a reference electrolyte chamber containing a liquid, reference electrolyte is formed, and which has, in a housing wall, especially an outer wall of the housing, a diaphragm permeable for the reference electrolyte for providing an electrolytic contact between the reference half cell and the measured medium;
 a potential indicating element extending into the reference electrolyte; and
 a supply opening opening into the reference electrolyte chamber for the supply of reference electrolyte into the reference electrolyte chamber;
wherein the reference half cell further includes a check valve blocking exit of reference electrolyte from the reference electrolyte chamber through the supply opening, especially a check valve arranged at least partially within the supply opening.

A check valve, also referred to as a one-way valve, blocks passage of a medium in a direction referred to as the blocking direction, while it permits passage in the opposed direction referred to as the flow direction of the check valve. Usually, check valves are so embodied, that a minimum pressure, also referred to as the breakthrough pressure or opening pressure, acting in the flow direction is required, after which the valve responds, i.e. lets medium flow in the flow direction.

Connected to the supply opening can be a reference electrolyte line, via which reference electrolyte can be replenished into the reference electrolyte chamber. Since the check valve blocks exit of reference electrolyte from the reference electrolyte chamber through the supply opening, contamination of the environment or a service person, upon the separating of the supply opening into the reference electrolyte chamber from the reference electrolyte line, is effectively excluded.

The supply opening into the reference electrolyte chamber can be, in the simplest case, a passageway in the outer wall of the housing of the reference half cell. The check valve can then be arranged, at least partially, within the passageway. In an embodiment, the check valve can have, for example, a ball shaped, closing body, which closes the passageway from the interior of the reference electrolyte chamber, and which, through an elastic element, for example, a spring, which is supported on a housing wall or another area arranged in the housing interior, is biased against the opening of the passageway into the reference electrolyte chamber. The opening pressure of such a check valve corresponds then to the opposing force, which the elastic element exerts on the closing body. The blocking direction of the check valve coincides with the direction pointing from the interior of the reference electrolyte chamber through the bore to the environment of the measuring probe. This embodiment is especially space saving.

If the reference electrolyte chamber has, for example, a rotationally symmetric shape, especially a cylindrical shape or the shape of an annular chamber, and if the bore extends through the housing wall radially to the imaginary rotational axis of the reference electrolyte chamber, then the blocking direction of the check valve points radially in the direction toward the measuring probe environment.

The supply opening can in another embodiment be formed by having a reference electrolyte duct opening into the reference electrolyte chamber, especially a hose connection nozzle drawn from the housing wall. In this case, the check valve can be arranged within the reference electrolyte duct and permit a liquid flow in the direction of the reference electrolyte chamber, while, however, blocking a liquid flow in the opposing direction, i.e. out from the reference electrolyte chamber. The check valve can also in this embodiment as in the case of the earlier described embodiment comprise a closing body biased from the interior of the reference electrolyte chamber against the opening of the supply opening into the reference electrolyte chamber.

The measuring half cell can comprise, for example, a pH glass electrode, a pH semiconductor electrode, especially a pH ISFET, an ion-sensitive electrode for measuring the concentration of cations, such as sodium-, potassium-, or calcium-ions or anions, such as chloride, fluoride, nitrate and carbonate. Serving as measuring membrane in the case of a glass electrode for pH value determining is an $H^+$-ion selective, glass membrane. In the case of ion-selective electrodes, also frequently applied are ion-selective, polymer membranes. The reference half cell can comprise an Ag/AgCl electrode, a calomel electrode or another conventional, reference electrode. Thus, an example of a reference electrolyte is 3-molar aqueous potassium chloride solution.

In an embodiment, means are present for effecting flow of the reference electrolyte out of the reference electrolyte chamber through the diaphragm. This has the advantage, that a penetration of contaminating substances through the diaphragm into the reference electrolyte chamber by diffusion or convection from the measured medium is prevented. This means can especially be means for pressurizing the reference electrolyte chamber. The pressure can occur during measurement operation of the measuring probe through the hydrostatic pressure of a liquid column of the reference electrolyte. It is, however, also possible to supply the reference electrolyte chamber via an additional connection with a pressurizing medium, e.g. pressurized air, or, via the supply opening into the reference electrolyte chamber, to supply reference electrolyte under pressure. For example, the reference electrolyte chamber and the therein located reference electrolyte can be supplied with a positive pressure of 0.2 to 0.5 bar, this meaning thus that the reference electrolyte flows slowly, however, steadily, through the diaphragm out into the measured medium.

The measuring probe can be embodied as a single-rod, measuring chain. The single-rod, measuring chain includes a measuring half cell and a reference half cell, especially according to one of the previously described embodiments.

The measuring half cell can have a first, especially tubular, housing part, which is sealed at a first end section by means of a measuring membrane liquid-tightly for forming an inner electrolyte chamber, in which an inner electrolyte is accommodated, into which extends a potential indicating element for sensing the potential established at the measuring membrane, and wherein the reference electrolyte chamber is formed, especially as an annular chamber, between the first, especially tubular, housing part, and a second, especially tubular, housing part surrounding the first, especially tubular, housing part, and connected with the first housing part in the region of the measuring membrane.

The inner electrolyte can be an aqueous, salt solution, for example, an aqueous potassium chloride solution, or, in the case of a pH measuring half cell, for example, a buffer solution.

The reference half cell can furthermore include a fill level sensor, which monitors the fill level of the reference electrolyte in the reference half cell. Using a control apparatus accommodated, for example, within the probe or outside the measuring probe, for example, in a measurement transmitter, and connected with the fill level sensor for data communication, the refilling of reference electrolyte into the reference electrolyte chamber can be controlled by means of the fill level sensor.

The invention includes furthermore a filling arrangement for filling a reference electrolyte chamber of a reference half cell of an electrochemical measuring probe (1), especially a potentiometric, measuring probe, especially one embodied according to one of the previously described embodiments, wherein the reference half cell has a supply opening opening into the reference electrolyte chamber, with a check valve blocking exit of reference electrolyte from the reference electrolyte chamber through the supply opening, especially a check valve arranged at least partially within the supply opening, which filling arrangement includes:
 a reference electrolyte supply container;
 a probe holder, in which a receptacle embodied for accommodating the measuring probe, especially for holding and/or affixing the measuring probe, is formed,
 a reference electrolyte line opening on one end into the reference electrolyte supply container and on the other end into the receptacle and being, toward the receptacle, closable by a valve mechanism, wherein the valve mechanism is embodied in such a manner that, upon introduction of the measuring probe into the receptacle, it interacts with the measuring probe, in order to provide a connection between the reference electrolyte line and the supply opening of the measuring probe, wherein the filling arrangement furthermore includes means for pressurizing reference electrolyte contained in the receptacle-side end region of the reference electrolyte line.

The measuring probe can be embodied as previously described. Since the valve mechanism is embodied in such a manner that, in the case of introduction of the measuring probe into the receptacle of the probe holder, it interacts with the measuring probe, in order to provide a connection between the reference electrolyte line and the supply opening of the measuring probe, by the introduction of the measuring probe into the receptacle, automatically a connection between the reference electrolyte line of the filling arrangement and the supply opening of the reference half cell of the measuring probe can be produced, so that reference electrolyte can be introduced from the reference electrolyte supply container via the reference electrolyte line and the supply opening of the reference half cell into the reference electrolyte chamber. Preferably, the valve mechanism includes sealing elements, which seals the so produced connection fluid-tightly relative to the environment, especially relative to the receptacle of the sensor holder.

In a state separated from the measuring probe, the valve mechanism can be closable, especially automatically, upon the removing of the measuring probe from the receptacle, in order so to close the reference electrolyte line and prevent escape of reference electrolyte into the environment.

The valve mechanism is operable mechanically, electrically, hydraulically, pneumatically, electromagnetically or piezoelectrically. In an advantageous embodiment, the actuatable valve mechanism interacts with the measuring probe in such a manner that, upon insertion of the measuring probe into the receptacle, the valve mechanism opens the receptacle-side opening of the reference electrolyte line, in order to form a liquid conveying connection between the reference electrolyte line and the supply opening of the reference half cell of the measuring probe, while, in the case of the removing of the measuring probe from the receptacle, the valve mechanism closes the reference electrolyte line.

For example, the valve mechanism can be mechanically actuatable, in that it is actuated positively by the introduction, or insertion, of the measuring probe into the receptacle. For this, the valve mechanism can comprise a movable element, whose movement effects a closing or opening of the reference electrolyte line opening into the receptacle, wherein the measuring probe and the movable element have complementary driving means, as for example, at least one driving pin and a thereto complementary, at least one guide pin, or a first abutment surface and a second abutment surface complementary to the first.

The valve mechanism can comprise an insert sleeve arranged in the receptacle movably along an imaginary longitudinal axis of the receptacle and having a first end, annular area, on which an elastic element directly or indirectly acts, wherein the insert sleeve has a passageway extending radially with respect to the longitudinal axis of the receptacle, and wherein the elastic element provides a restoring force acting on the insert sleeve in the axial direction, when the insert sleeve is so positioned, that the passageway aligns with the reference electrolyte line opening into the receptacle.

The elastic element can be an elastic body, especially an elastic spring, e.g. a helical spring. Preferably, the elastic body is so arranged, that it provides a restoring force in the axial direction in the case of deflection from its rest position, for example, by compression or extension. The elastic element can act directly on the end face of the insert sleeve or indirectly, e.g. exerted via one or a number of other intermediate components. The insert sleeve can be secured by guiding means in the receptacle against twisting relative to the receptacle and/or the measuring probe.

In the rest position of the elastic element, the radial passageway of the insert sleeve, on whose first end, annular area of the elastic element acts, aligns, preferably, not with the reference electrolyte line, so that the reference electrolyte line is sealed relative to the receptacle.

In an embodiment, the insert sleeve can have a second end, annular area, which serves as an opposing surface for an abutment surface of the measuring probe. In this embodiment, the opening of the reference electrolyte line into the receptacle is sealed by the insert sleeve, when no measuring probe is in the receptacle. Upon insertion of the measuring probe into the receptacle, the abutment surface of the measuring probe leads the second end, annular area of the measuring probe in the direction of the insertion movement of the measuring probe. Through the movement of the insert sleeve, the elastic element is deflected from its rest position, i.e. biased, and exerts so a restoring force on the insert sleeve, so that the insert sleeve is biased against the abutment surface of the measuring probe.

In an additional embodiment, the receptacle has an internal thread, which is so embodied, that it forms a screw thread connection with a external thread of the measuring probe complementary to the internal thread, in order to affix the measuring probe in the receptacle. The internal thread and the complementary external thread are preferably so embodied, e.g. by stops, that the supply opening of the reference half cell in the end position of the measuring probe in the receptacle aligns with the receptacle-side opening of the reference electrolyte line and the passageway of the insert sleeve.

The means for pressurizing the reference electrolyte contained in the receptacle-side end region of the reference electrolyte line can have a connection nozzle of the reference electrolyte supply container for the delivery of a pressurizing medium, e.g. pressurized air, into the reference electrolyte supply container and/or into the reference electrolyte line. The means permit preferably the supplying of the reference electrolyte with a pressure, which exceeds the opening pressure of the check valve of the measuring probe.

In a further development, the filling arrangement can include a pressure sensor, which registers the pressure reigning in the reference electrolyte supply container and outputs such as a measured value. On the basis of the pressure measured value, the pressure within the supply container and correspondingly the pressure of the electrolyte filled into the reference electrolyte chamber of the measuring probe can be monitored, and be adjusted, manually or automatically with the assistance a control apparatus, e.g. a microcontroller, to a constant value. The pressure sensor can, for example, be arranged directly within the reference electrolyte supply container or within a supply line, or drain, of the reference electrolyte supply container, especially within the delivery line for the pressurizing medium or within the reference electrolyte line. In the reference electrolyte supply container, there can supplementally or alternatively be arranged also a fill level sensor, which monitors the amount of the electrolyte contained in the reference electrolyte supply container. By means of a, or the, control apparatus, the fill level in the reference electrolyte supply container can be monitored, and, when required, e.g. when the fill level subceeds, or falls beneath, a predetermined limit value, an alarm can be issued. The control apparatus can be a component of an electronics arranged within the filling arrangement, of a sensor electronics arranged within the measuring probe, for example, within a probe plug head, or of a superordinated unit, for example, a measurement transmitter, with the measuring probe and/or the filling arrangement, especially connectable for data exchange.

An assembly device, for instance a retractable assembly device, for connecting the measuring probe to a process container, can include a filling arrangement according to one of the previously described embodiments. The process container can be e.g. a pipe, in which a reactant, or product, stream of a chemical or treatment process is conveyed.

Through insertion of a measuring probe according to one of the previously described embodiments into a filling arrangement according to one of the previously described embodiments, a measuring arrangement is formed, which includes an electrochemical, especially potentiometric, measuring probe for measuring a chemical or physical, measured variable, especially a pH value, of a measured medium, and a filling arrangement, wherein the measuring probe has at least one reference half cell and at least one measuring half cell, wherein the reference half cell includes:
- a housing of electrically insulating material, in which is formed a reference electrolyte chamber containing a liquid, reference electrolyte, and which has in a housing wall a diaphragm permeable for the reference electrolyte for providing an electrolytic contact between the reference half cell and the measured medium,
- a potential indicating element extending into the reference electrolyte, and
- a supply opening into the reference electrolyte chamber for the supply of reference electrolyte into the reference electrolyte chamber, wherein the reference half cell has a check valve blocking exit of reference electrolyte from the reference electrolyte chamber through the supply opening, especially a check valve arranged at least partially within the supply opening, and wherein the filling arrangement includes:
- a reference electrolyte supply container,
- a probe holder, in which is formed a receptacle for accommodating the measuring probe, especially one embodied for holding and/or affixing the measuring probe,
- a reference electrolyte line opening on one end into the reference electrolyte supply container and on the other end into the receptacle, and closable toward the receptacle by a valve mechanism, wherein the valve mechanism is embodied in such a manner that, in the case of introduction of the measuring probe into the receptacle, it interacts with the measuring probe, in order to provide a connection between the reference electrolyte line and the supply opening of the measuring probe, wherein the filling arrangement furthermore includes means for pressurizing reference electrolyte contained in the receptacle-side end region of the reference electrolyte line.

Especially, the reference electrolyte contained in the reference electrolyte line can be provided with a pressure, which exceeds the opening pressure of the check valve arranged at least partially within the supply opening, so that the check valve permits inflow of reference electrolyte into the reference electrolyte chamber.

The measuring arrangement can in detail be embodied in the manner, in each case, individually described previously for measuring probe and the filling arrangement.

The invention relates furthermore to a maintenance arrangement for maintenance of measuring probes, especially measuring probes according to one of the described embodiments, wherein the maintenance arrangement comprises: A maintenance system for maintaining the measuring probes, wherein the maintenance system includes a filling arrangement according to one of the previously described embodiments. The maintenance system can furthermore include a calibration system for calibrating the measuring probes, wherein the calibration system includes, especially, at least one container containing a calibration liquid with a defined pH value.

In an advantageous embodiment, the maintaining of the measuring probes in the maintenance arrangement can occur automatically, especially by means of a control system, which includes, for example, a microcontroller, in which, especially, measuring probe specific, maintenance programs are stored. In this embodiment, the maintenance system can furthermore comprise:

A storage system for storage of measuring probes;
a handling system; and
a control system for control and monitoring of the storage system, the handling system and the maintenance system, wherein the handling system includes means for transporting the measuring probes, especially from the storage system to the maintenance system or within the maintenance system, e.g. between different stations of the maintenance system.

The terminology, 'maintenance of measuring probes', especially pH or ion-selective measuring probes, means here and in the following especially the cleaning and calibrating of the measuring probes.

The measuring probes can include a memory module, which contains measuring probe specific data. The measuring probe specific data can be read-out by the control system, wherein the control system, on the basis of the data read-out, ascertains the maintenance measures to be performed and correspondingly controls the handling system, so that the measuring probe passes through the maintenance system and experiences the ascertained maintenance measures there.

BRIEF DESCRIPTION OF THE DRAWINGS

The invention will now be explained in greater detail on the basis of the example of an embodiment illustrated in the drawing, the figures of which show as follows.

DETAILED DISCUSSION IN CONJUNCTION WITH THE DRAWINGS

Figure 1:
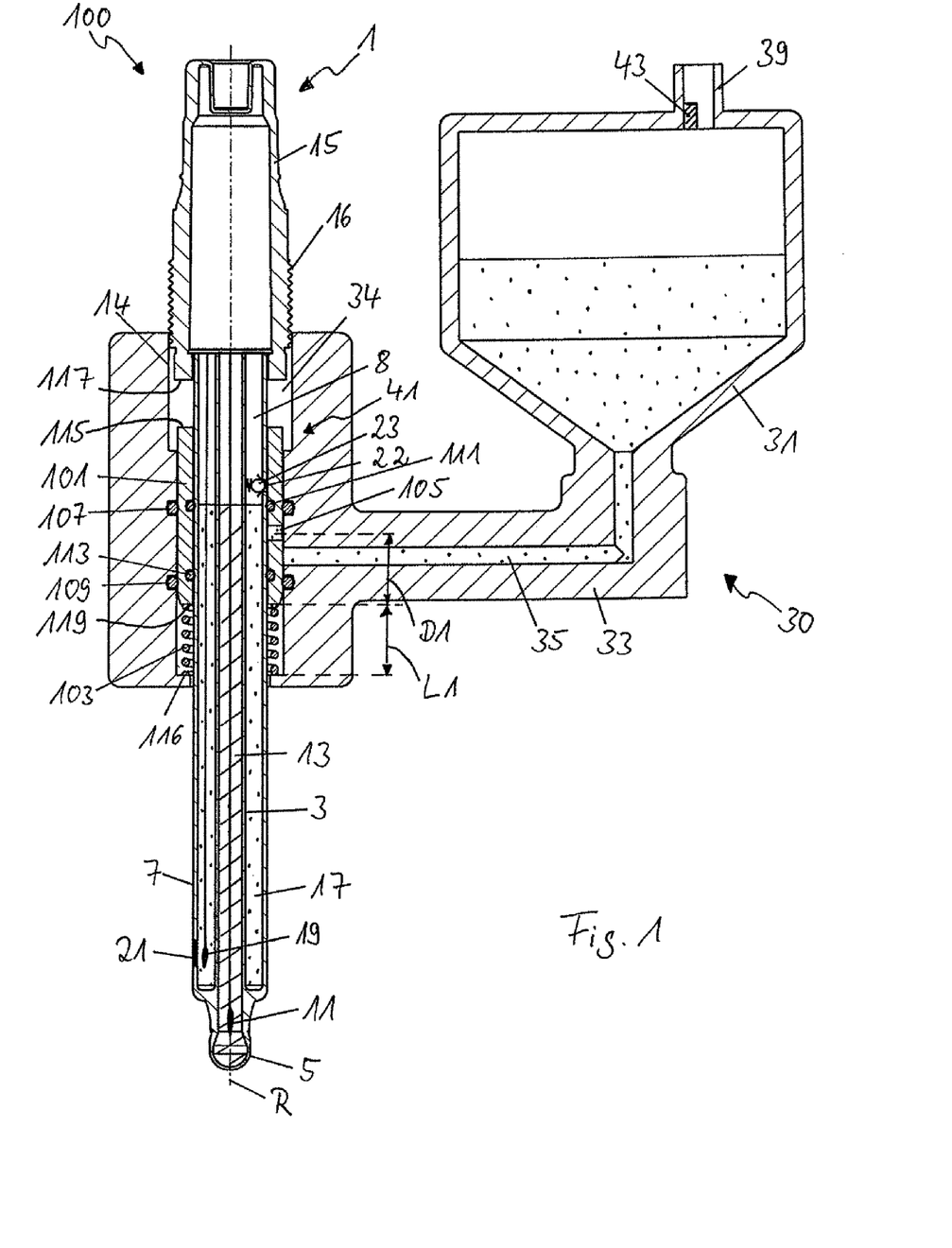
FIG. 1 is a filling arrangement and a potentiometric measuring probe in a position showing introduction thereof into a receptacle of the filling arrangement.
Figure 2:
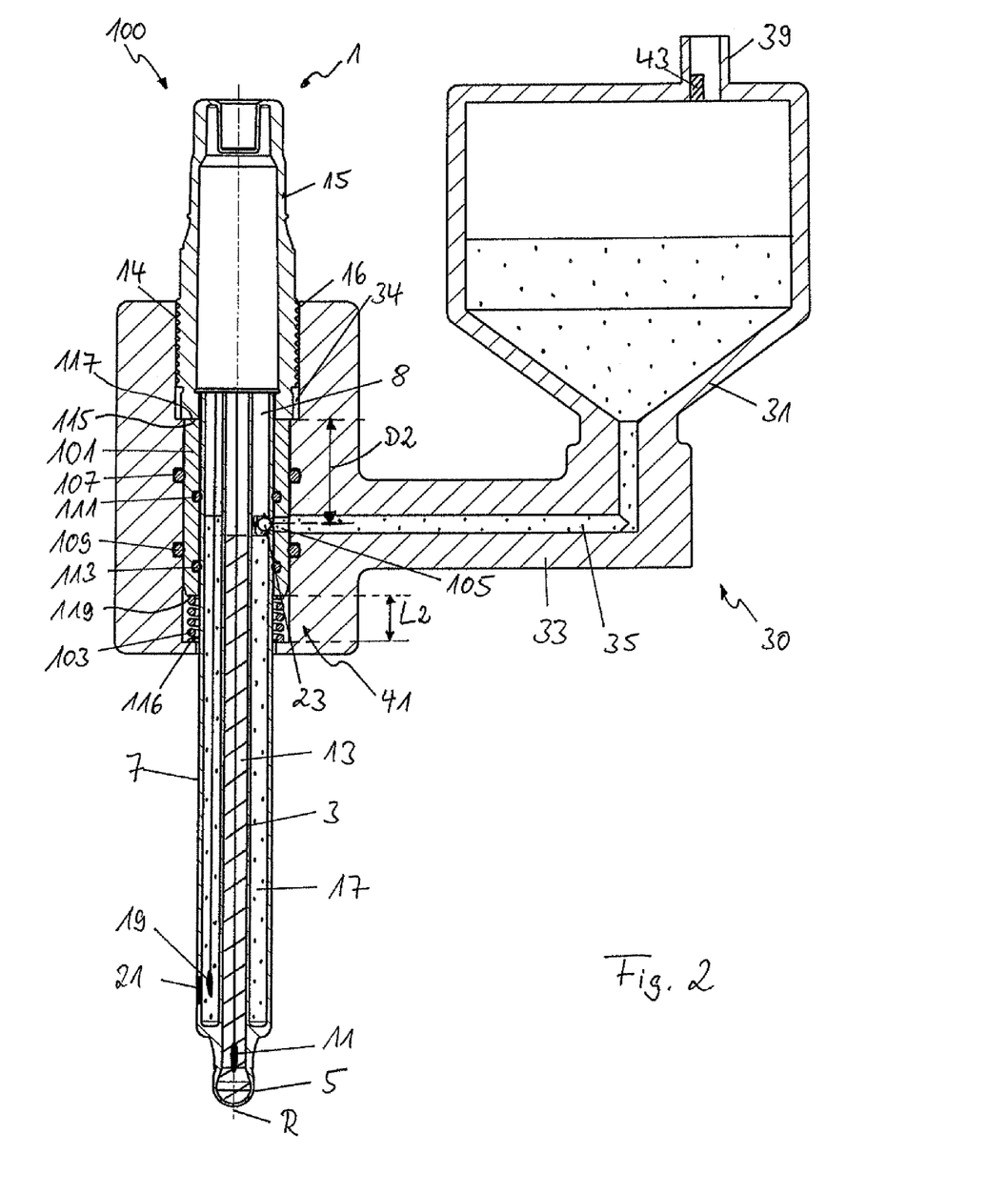
FIG. 2 the measuring probe accommodated in the filling arrangement.

Presented in FIGS. 1 and 2 is a measuring arrangement 100, which includes a measuring probe 1 and a filling arrangement 30. The measuring probe 1 is in the representation the FIG. 1 partially inserted into a receptacle 34 formed in the filling arrangement 30, but has not yet reached its end position, where it becomes secured in the receptacle 34. FIG. 2 shows the same measuring probe 1 in its end position in the filling arrangement 30, where it is secured in the receptacle 34.

The measuring probe 1 is a potentiometric measuring probe, in the example of FIG. 1 a pH glass electrode embodied as a single-rod, measuring chain and having a measuring half cell and a reference half cell. The measuring probe 1 possesses an electrically insulating housing, for example, of glass, which has an inner tube 3, which is terminated on an end by a measuring membrane 5, in the present example a pH sensitive, glass membrane. The inner tube 3 is surrounded by an electrically insulating, outer tube 7, which is connected with the inner tube 3 in its end region facing the glass membrane 5, so that a ring-shaped, reference electrolyte chamber 8 is formed extending around the inner tube 3. Reference electrolyte chamber 8 is completely liquid-tightly separated and electrically insulated from the housing interior of the inner tube 3.

The housing interior of the inner tube 3 surrounded by the glass membrane 5 and the inner tube 3 is filled with a solution 13 of known pH value for buffering the pH value. Extending into solution 13 for sensing the potential is a potential sensing element 11, which is formed, for example, of a chlorided, silver wire. The so formed measuring half cell of the measuring probe 1 is electrically connected via the potential sensing element 11 with an electrical or electronic circuit (not shown) in the connection head 15 of the measuring probe 1. The reference electrolyte chamber 8 surrounded by the inner tube 3 and the outer tube 7 is filled with a liquid, reference electrolyte 17, for example, a 3-molar aqueous potassium chloride solution. Into the reference electrolyte extends a potential sensing element 19, which, like the potential sensing element 11, can be embodied as a silver wire coated with silver chloride. Arranged in the outer tube 7 is a diaphragm 21, which enables an exchange of charge carriers between the reference electrolyte chamber 8 bounded by the outer tube 7 and the environment, for example, a measured medium, in which the measuring probe 1 is immersed. Diaphragm 21 can be formed, for example, by a circular disk of porous ceramic. The so formed reference half cell of the measuring probe 1 is connected via the potential sensing element 19 electrically conductively with the circuit in the connection head 15. The circuit transduces and processes the potentials delivered by the potential sensing elements 11 and 19 and forwards the conditioned signals. It can form, for example, at least one part of the measuring electronics for the conversion and processing of the measuring probe signal, and so, among other things, comprise means for determining potential difference between the potential of the measuring half cell and the potential of the reference half cell. The measuring electronics is, thus, in this example, at least partially, accommodated in the connection head 15. A further part of the measuring electronics can be accommodated in a superordinated unit, e.g. a measurement transmitter, connected with the connection head 15 of the measuring probe 1. Alternatively, also the entire measuring electronics can be accommodated in the measurement transmitter. In this case, the electrical or electronic circuit in the connection head serves only for forwarding signals of the measuring probe 1 to the measurement transmitter.

In measurement operation, the measuring probe 1 is immersed in a measured medium (not drawn). The region of the housing outer wall of the measuring probe 1, which, in such case, comes in contact with the measured medium, is referred to as the immersion region. This immersion region includes both the measuring membrane 5 as well as also the diaphragm 21. In the measuring probe 1, a temperature sensor (not shown) can optionally be provided.

In a region lying preferably outside the immersion region, the outer tube 7 has a supply opening 22, through which reference electrolyte 17 can be replenished into the reference electrolyte chamber 8. Supply opening 22 is in the present example embodied as a passageway bore extending, as regards the imaginary cylinder axis R of the outer tube, radially through the wall of the outer tube. Arranged in the supply opening 22 on its reference electrolyte chamber side is a check valve 23, which blocks exit of reference electrolyte 17 through the supply opening 22. In the present example, the blocking direction of the check valve 23 is thus directed, as regards the imaginary cylinder axis R of the cylindrically symmetrical reference electrolyte chamber 8, radially outwards, and so blocks exit of reference electrolyte 17 from the reference electrolyte chamber 8 into the environment.

The check valve 23 can be embodied, for example, as a ball check valve or a disk check valve. In the case of these types of check valves, a ball or a disk is biased against an opening by means of an elastic element, for example, a spring, delivering a restoring force. In this way, passage of a medium, especially a liquid, through the opening in the direction of the restoring force is blocked. In the opposing direction, medium can move through the valve and, correspondingly, through the opening, once it overcomes the restoring force acting on the ball or disk. The pressure, which the medium must exert against the check valve in the flow direction, in order to overcome this restoring force, is referred to as the breakthrough pressure, or opening pressure. The check valve 23 blocks, thus, on the one hand, exit of liquid from the reference electrolyte chamber 8, permits, however, on the other hand, the filling and refilling of reference electrolyte 17 into the reference electrolyte chamber 8.

In order to prevent during measurement operation a penetration of reference electrolyte contaminating or diaphragm plugging substances from the measured medium into the reference electrolyte chamber 8 via the diaphragm 21, the reference electrolyte 17 present in the reference electrolyte chamber 8 is provided with a positive pressure relative to the environment, i.e. especially relative to the measured medium. The positive pressure is so selected that, during measurement operation, i.e., in the case of immersion of the measuring probe 1 into a measured medium for determining a physical or chemical, measured variable of the medium, e.g. pH value, continuously, a small amount of reference electrolyte 17 escapes through the diaphragm 21 into the measured medium. For producing a sufficient excess pressure, either the hydrostatic pressure of the liquid column within the reference electrolyte chamber 8 can be utilized, or the reference electrolyte chamber 8 can be supplied supplementally with pressure by supplying a pressurizing medium, e.g. air. The pressurizing medium can be introduced into the reference electrolyte chamber 8 e.g. in the filling of the reference electrolyte chamber 8 with reference electrolyte 17. Alternatively, the reference electrolyte chamber 8 can also have a separate connection for the delivery of a pressurizing medium. Another opportunity is to supply the reference electrolyte 17 into the reference electrolyte chamber 8 under pressure via the supply opening 22.

The connection head 15 can be embodied as a sensor plug head, which forms the primary side of a pluggable connector coupling. Via the pluggable connector coupling, the single-rod, measuring chain can be connected with a superordinated unit, for example, a measurement transmitter. The conditioned signals can be transmitted to the superordinated unit and there further processed and/or output. The pluggable connector coupling can be embodied as a plug contact with galvanic coupling, or, for minimizing electrical disturbing influences, as a plugged connection with inductive signal- and energy transmission.

The filling arrangement 30 serves for replenishing liquid, reference electrolyte 17 into the reference electrolyte chamber 8 of the measuring probe 1. The filling arrangement includes a reference electrolyte supply container 31, in which a supply of reference electrolyte 17 is accommodated. Furthermore, the filling arrangement 30 includes a receptacle 34 embodied as a seating tube, in which the measuring probe 1 can be held and mechanically secured; compare FIG. 2. For this, the receptacle 34 includes an internal thread 14 complementary to an external thread 16 of the connection head 15 of the measuring probe 1. Alternatively, the receptacle 34 can also possess a connection nozzle, to which the connection head 15 is affixable by means of an union nut. The supply vessel 31 is connected, via a reference electrolyte line 35 formed as a duct in the receptacle apparatus 33, with the reference electrolyte chamber 8 of the measuring probe 1. The filling arrangement 30 can be, for example, a component of an assembly apparatus (not shown), for example a retractable assembly, which connects the measuring probe 1 with a process container containing the measured medium, and which, during measurement operation, positions the measuring probe 1 in such a manner, that it extends with its immersion region into the measured medium.

In the region of the opening of the reference electrolyte line into the receptacle 34, the filling arrangement 30 possesses a valve mechanism 41, which, depending on position, permits or blocks exit of reference electrolyte 17 from the reference electrolyte line 34. The valve mechanism 41 includes an insert sleeve 101, which is shiftable within the receptacle in the axial direction, i.e. along the imaginary cylinder axis of the seating tube forming the receptacle 34, coinciding with the imaginary cylinder axis R of the measuring probe 1. The insert sleeve 101 has a passageway 105, which extends radially relative to the imaginary cylinder axis of the receptacle 34 coinciding with the imaginary cylinder axis of the insert sleeve and which ideally has essentially the same cross section as the reference electrolyte line 35.

Acting on a first end, annular area 119 of the insert sleeve 101 is a helical spring 103, which is supported on its end away from the insert sleeve 101 on a shoulder 116 formed by a cross sectional narrowing of the seating tube. In such case, the helical spring 103 and the insert sleeve 101 are so embodied, that the sum of the length L1 of the helical spring 103 in its resting state and the distance D1 of the passageway 105 from the first end, annular area 119 of the insert sleeve 101 is greater at least by the diameter of the passageway 105 than the distance of the opening of the reference electrolyte line 35 into the receptacle 34 from the shoulder 116 the seating tube, on which the helical spring 103 is supported. In this way, the passageway 105 is arranged offset relative to the opening of the reference electrolyte line 35 into the receptacle 34, when the helical spring 103 is in its rest position. This position of the insert sleeve 101, which corresponds to the closed position of the valve mechanism 41, is shown in FIG. 1.

The section of the receptacle 34, in which, in the rest position of the helical spring 103, the passageway 105 of the insert sleeve 101 and the opening of the reference electrolyte line 35 into the receptacle 34 are located, is sealed from both openings of the receptacle 34 by means of seals 107, 109, which are arranged in annular grooves of the seating tube encircling the cylinder axis R. In this way, it is assured, that neither from the reference electrolyte line 35 nor from the passageway 105 can reference electrolyte 17 escape into the environment, when no measuring probe 1 is in the receptacle 34, or when the measuring probe 1, as in FIG. 1, is still not completely inserted into the receptacle 34.

The connection head 15 of the measuring probe 1 includes on its end facing the measuring membrane 5 a membrane-end, annular area 117 perpendicular to the cylinder axis R. In the case of the introduction of the measuring probe 1 into the receptacle 34 of the filling arrangement 30, or into the insert sleeve 101, this end area 117 abuts on a second end, annular area 115 of the insert sleeve 101 facing away from the spring 103 and so forms an opposing surface for the insert sleeve 101. The distance D2 between the passageway 105 of the insert sleeve 101 and the second end, annular area 115 is equal to the distance between the supply opening 22 of the reference half cell and the membrane end, annular area 117 of the connection head 15 of the measuring probe 1. Thus is assured, that the supply opening 22 and the passageway 105 align with one another, when the measuring probe is seated in the receptacle 34 of the filling arrangement; compare FIG. 2. When the measuring probe 1 is seated, the passageway 105 is sealed toward both end faces of the insert sleeve 101 with seals 111, 113, which are arranged in annular grooves of the insert sleeve 101 encircling the cylinder axis R.

Through further shifting of the measuring probe 1 in the axial direction, in order to bring the measuring probe 1 into its end position in the receptacle 34, the insert sleeve 101 is axially shifted against the helical spring 103. Through this movement, the helical spring 103 is compressed to a length L2 and therewith deflected from its rest position; compare FIG. 2. Through the deflection from the rest position, there arises a restoring force acting in the axial direction toward the connection head 15 of the measuring probe. This biases the insert sleeve 101 against the opposing surface formed by the membrane-end, annular area 117 of the connection head 15.

The axial shifting of the insert sleeve 101, in the shifting of the measuring probe 1 into its end position, brings the passageway 105 in the insert sleeve 101 and the opening of the reference electrolyte line 35 into the receptacle 34 into alignment, so that reference electrolyte 17 can enter from the reference electrolyte line 35 into the passageway 105. Stops and guiding means can be provided, in order to avoid a twisting of the measuring probe 1, the insert sleeve 101 and the receptacle 34 around the axis R relative to one another. In a possible variant, in the region of the opening of the reference electrolyte line 35 into the receptacle 34, a surrounding cavity serving as an annular chamber between the receptacle 34 and the insert sleeve 101 can be provided in the seating tube forming the receptacle 34. If the measuring probe 1 is secured in its end position in the receptacle 34, then the reference electrolyte line 35 and the passageway 105 of the insert sleeve 101 open into the annular duct, so that a connection open for the reference electrolyte is formed between the reference electrolyte line 35 and the passageway 105. When the measuring probe 1 is accommodated in its end position in the receptacle 34 and secured by means of the screw thread connection 14, 16, the reference electrolyte line, the passageway 105 and the supply opening 22 align with one another. The reference electrolyte 17 acts then on the check valve 23. This corresponds to the opened position of the valve mechanism 41.

In this position, i.e. in the case of opened valve mechanism 41, reference electrolyte 17 can flow from the reference electrolyte supply container 31 via the reference electrolyte line 35 into the reference electrolyte chamber 8, since the reference electrolyte 17 passes the check valve 23 in the flow direction, as soon as the pressure exerted by the reference electrolyte 17 on the check valve 23 overcomes the restoring of force of the check valve 23, i.e. as soon as the opening pressure of the check valve 23 is exceeded. The reference electrolyte supply container 31, or the fill level of the reference electrolyte 17 accommodated in the reference electrolyte supply container can especially be arranged so high relative to the check valve 23, that the hydrostatic pressure of the reference electrolyte 17 is sufficient to overcome the opening pressure of the check valve.

If the measuring probe 1, conversely, is removed from the receptacle 34, the restoring of force of the helical spring 103 effects an axial movement of the insert sleeve 101 back into the position shown in FIG. 1, in which the helical spring 103 reaches its rest position and therewith its length L1. In this way, the passageway opening 105 is shifted relative to the reference electrolyte line 35 and therewith the opening of the reference electrolyte line 35 is sealed. By means of the seals 107 and 109 arranged in the annular grooves of the seating tube forming the receptacle 34, the opening of the reference electrolyte line 35 relative to the receptacle 34 and therewith relative to the environment is sealed. The valve mechanism 41 thus closes automatically, upon the removing of the measuring probe 1 from the receptacle 34. Thus, a contamination of the environment or of a service person with escaping reference electrolyte 17 is completely excluded.

The reference electrolyte supply container 31 includes a connection nozzle 39, via which it can be connected with a supply of a pressurizing medium, for example, a pressurized air line. In this way, the reference electrolyte 17 can be replenished into the reference electrolyte chamber 8 of the measuring probe 1 with a positive pressure, preferably an adjustable positive pressure. By means of a pressure measuring transducer 43 arranged in the region of the connection nozzle 39, the pressure within the supply container can be monitored and, on the basis of the pressure measuring transducer signal, in given cases, controlled, e.g. to a constant value above the opening pressure of the check valve 23.

The filling arrangement 30 can be a component of an assembly device, for instance a retractable assembly, by means of which the measuring probe 1 can be introduced into a measured medium located in a process container. Then, also during measurement operation of the measuring probe 1, continuously or in certain time intervals, reference electrolyte 17 can be replenished into the reference electrolyte chamber 8.

Alternatively, the refilling of reference electrolyte 17 by means of the filling arrangement 30 can, however, also be performed in the context of maintenance measures, which are performed spatially separated from the measuring point, for example, in a laboratory. Examples of such maintenance measures are calibrating, cleaning and regeneration of electrochemical measuring probes. For this, the filling arrangement 30 can be a component of a calibration station. The calibration station includes, besides the filling arrangement 30, in which the measuring probe 1 is accommodated for performing the calibrating, at least one container having a calibration liquid of defined pH value, preferably, however, a number of containers with a plurality of calibration liquids of different, defined pH values. For calibrating, the connection head 15 of the measuring probe 1 is connected with a superordinated unit, e.g. a measurement transmitter, which contains a measuring electronics, which is embodied to process further, in pH values to convert and to output the measuring probe signals output by the electrical or electronic circuit arranged in the connection head.

The measuring probe 1 can have in its connection head especially a microcontroller with a memory module. The memory module can contain, for example, one or a number of the following data: Calibration data, especially zero-point and slope of the measuring probe signal, earlier calibrations of the measuring probe, offset data, slope data, compensation coefficients, data regarding cross sensitivities, temperature dependences, allowable extreme values of parameters, such as e.g. pressure and temperature, loading-relevant for measuring probe, actually arisen extreme values, duration of operation of the measuring probe, measuring location identification, measuring probe identification, etc. In the case of a measuring probe of a pH sensor, for example, the following datacan be contained in the memory module: The ascertained sensitivity of the measuring probe at a first temperature, especially $25_tC$, the ascertained asymmetry potential at $25_tC$, temperature offset, logistical information, temperature use range, the pH field of use, extreme values of operating temperature, extreme values of operating pH value, period of use, isothermal intersection point, zero point and slope of the pH value, probe signal as calibration parameters.

Figure 3:
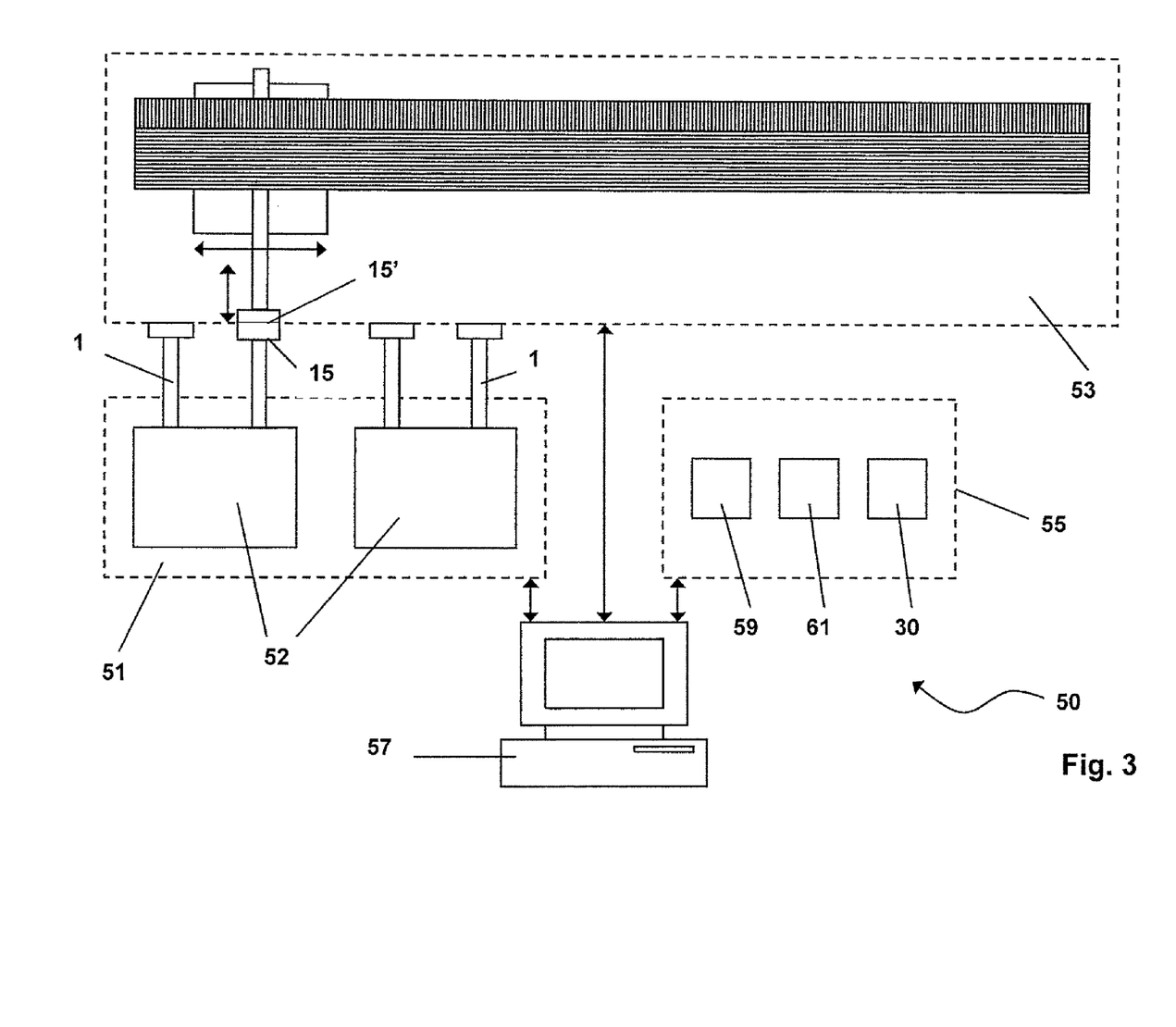
FIG. 3 is a schematic representation of a maintenance unit for maintenance of measuring probes.

For measuring probes, which possess a memory module for storing such data, advantageously, an automatic maintenance arrangement 50, such as that shown schematically in FIG. 3, can be used. The maintenance arrangement 50 includes a storage system 51, a handling system 53, a maintenance system 55 and a control system 57. The handling system 53 transports the measuring probes 1 from the storage system 51 into the maintenance system 55. Robotic elements can be applied. The control system 57 controls the handling system and the maintenance system. It controls the course of events, with which the measuring probes 1 are subjected to maintenance. For this, the control system 57 reads the required data either from the memory module of a measuring probe 1 or from a database, after a measuring probe 1 has been identified as being a known type of probe.

The storage system 51 includes at least one container 52, in which the measuring probes can be stored without damage. The maintenance system 55 includes a cleaning system 59 and a calibration system 61 as well as the filling arrangement 30 described on the basis of FIGS. 1 and 2. The cleaning system 59 has cleaning agent available, which, in given cases, are matched to, and individually established for, the type of fouling. It includes at least one cleaning chamber, in which the measuring probe 1 is exposed to a cleaning agent. This can occur by immersion, rinsing or spraying, wherein also combinations and multiple sequences thereof are options. Additionally, a heat-, brushing-, or ultrasound treatment can occur. The calibration system 61 includes, like the previously described cleaning system, one or a number of containers containing one or a plurality of calibration liquids, which have defined pH values.

A measuring probe 1 to be maintained is taken by the handling system 53. For this, the connection head 15 of the measuring probe 1 is connected with a corresponding holder 150 of the handling system 53. Through the connection, also a connection via a galvanic or inductive coupling of the electronics accommodated in the connection head 15 with the control system is produced, so that data stored in the memory module of the connection head 15 can be read-out by the control system 57, or new data stored by the control system 57 into the memory module of the measuring probe 1.

The control system 57 establishes, on the basis of data read-out from the measuring probe 1, which maintenance steps should be performed in which sequence. Correspondingly, the control system 57 controls the handling system 53, for example, a transport robot with a gripping arm, which transports the measuring probe 1 through the individual stations of the maintenance system 55, e.g. cleaning, filling, calibrating. The maintained measuring probe 1 is then transported back into the storage system 51 and released from the holder 16 of the handling system 53. Then, the measuring probe 1 can be brought back to the process measuring point and there applied anew for measuring.

Structurally, it is especially an option, to construct the maintenance system 55 such that it is composed not of three stations, but, instead only of a single station, to which the different media for cleaning, calibrating and filling are conveyed. In this case, transport from station to station can be omitted.

The invention claimed is:

1. An electrochemical measuring probe, for measuring a chemical or physical, measured variable, of a measured medium, comprises:
   at least one measuring half cell; and
   at least one reference half cell, wherein:
   said reference half cell includes:
   a housing of electrically insulating material, in which a reference electrolyte chamber containing a liquid-reference electrolyte is formed, and which has in a housing wall a diaphragm permeable for the reference electrolyte for providing electrolytic contact between said reference half cell and said measured medium;
   a potential indicating element extending into the reference electrolyte;
   a supply opening opening into said reference electrolyte chamber for supply of reference electrolyte into said reference electrolyte chamber; and
   a check valve blocking exit of reference electrolyte from said reference electrolyte chamber through said supply opening.

2. The measuring probe as claimed in claim 1, wherein: the measuring probe is embodied as a single-rod, measuring chain.

3. The measuring probe as claimed in claim 2, wherein:
   said at least one measuring half cell has a first housing part, which is sealed liquid-tightly at a first end section by means of a measuring membrane for forming an inner electrolyte chamber;
   accommodated in said inner electrolyte chamber is an inner electrolyte, into which a potential indicating element extends for sensing potential at said measuring membrane; and
   said reference electrolyte chamber is formed, between said first housing part, and a second housing part, said second housing part surrounding said first housing part and connected with said first housing part in the region of said measuring membrane.

4. The measuring probe as claimed in claim 1, wherein:
   said first housing part and said second housing part have a tubular shape and said second housing part and said reference electrolyte chamber is formed as an annular chamber between said first housing part and said second housing part.

5. The measuring probe as claimed in claim 1, wherein:
   said supply opening comprises a passageway in the outer wall of the reference half cell, and said check valve comprises a closing body, which is biased against the opening of the passageway into the reference electrolyte chamber by means of an elastic element, which is supported on a housing wall or another area arranged inside the housing.

6. The measuring probe as claimed in claim 1, wherein:
   said measuring probe is embodied to effect a flowing out of reference electrolyte from said reference electrolyte chamber through said diaphragm.

7. The measuring probe as claimed in claim 6, wherein:
   said reference electrolyte chamber is pressurized for effecting flow of the reference electrolyte from said reference electrolyte chamber through said diaphragm by means of a hydrostatic pressure of a liquid column of said reference electrolyte.

8. The measuring probe as claimed in claim 6, wherein:
   said reference electrolyte chamber comprises a connection for supplying said reference electrolyte chamber with a pressurizing medium.

9. The measuring probe as claimed in claim 6, wherein:
   said reference electrolyte chamber is supplied with a positive pressure relative to the environment.

10. The measuring probe as claimed in claim 6, wherein:
    said reference electrolyte chamber is supplied with a positive pressure of 0.2 to 0.5 bar.

11. The measuring probe as claimed in claim 6, wherein:
said reference half cell including a fill level sensor, which monitors the fill level of the reference electrolyte in the reference half cell.

12. The measuring probe as claimed in claim 1, wherein:
said reference half cell including a fill level sensor, which monitors the fill level of the reference electrolyte in the reference half cell.

13. The measuring probe as claimed in claim 12, wherein:
said fill level sensor is connected with a control apparatus for data communication.

14. The measuring probe as claimed in claim 13, wherein:
said control apparatus is configured to control a refilling of reference electrolyte into the reference electrolyte chamber.

15. An electrochemical measuring probe, for measuring a chemical or physical, measured variable, of a measured medium, comprises:
at least one measuring half cell; and
at least one reference half cell, wherein:
said reference half cell includes:
a housing of electrically insulating material, in which a reference electrolyte chamber containing a liquid, reference electrolyte is formed, and which has in a housing wall a diaphragm permeable for the reference electrolyte for providing electrolytic contact between said reference half cell and said measured medium;
a potential indicating element extending into the reference electrolyte;
a supply opening opening into said reference electrolyte chamber for supply of reference electrolyte into said reference electrolyte chamber; and
a check valve blocking exit of reference electrolyte from said reference electrolyte chamber through said supply opening, and wherein:
said supply opening is connected to a reference electrolyte line, via which reference electrolyte can be replenished into said reference electrolyte chamber.

16. The measuring probe as claimed in claim 15, wherein:
said supply opening comprises a passageway in the outer wall of the reference half cell, and said check valve comprises a closing body, which is biased against the opening of the passageway into the reference electrolyte chamber by means of an elastic element, which is supported on a housing wall or another area arranged inside the housing.

17. The measuring probe as claimed in claim 15, wherein:
said measuring probe is embodied to effect a flowing out of reference electrolyte from said reference electrolyte chamber through said diaphragm.

18. The measuring probe as claimed in claim 17, wherein:
said reference electrolyte chamber is pressurized for effecting flow of the reference electrolyte from said reference electrolyte chamber through said diaphragm by means of a hydrostatic pressure of a liquid column of said reference electrolyte.

19. The measuring probe as claimed in claim 17, wherein:
said reference electrolyte chamber comprises a connection for supplying said reference electrolyte chamber with a pressurizing medium.

20. The measuring probe as claimed in claim 17, wherein:
said reference electrolyte chamber is supplied with a positive pressure relative to the environment.

* * * * *